United States Patent
Raidel et al.

(10) Patent No.: US 6,984,225 B2
(45) Date of Patent: Jan. 10, 2006

(54) ABSORBENT ARTICLE AND PROCESS FOR THE DIRECTED DRAINAGE OF FLUIDS RELEASED IN A LOCALIZED MANNER

(75) Inventors: Maria Raidel, Nürnberg (DE); Franz Aschenbrenner, Kastl (DE)

(73) Assignee: Hakle-Kimberly Deutschland GmbH, Koblenz (DE)

(*) Notice: Subject to any disclaimer, the term of this patent is extended or adjusted under 35 U.S.C. 154(b) by 0 days.

(21) Appl. No.: 09/855,045

(22) Filed: May 15, 2001

(65) Prior Publication Data

US 2001/0027305 A1 Oct. 4, 2001

Related U.S. Application Data

(63) Continuation of application No. 09/142,115, filed as application No. PCT/EP97/01144 on Mar. 6, 1997, now Pat. No. 6,241,714.

(30) Foreign Application Priority Data

Mar. 11, 1996 (DE) .......................... 196 09 462

(51) Int. Cl.
*A61F 13/15* (2006.01)

(52) U.S. Cl. .............................. 604/385.101; 604/378; 604/383

(58) Field of Classification Search ................ 604/378, 604/379, 380, 381, 382, 383, 384, 385.101
See application file for complete search history.

(56) References Cited

U.S. PATENT DOCUMENTS

| | | |
|---|---|---|
| 810,119 A | 1/1906 | Green |
| 810,130 A | 1/1906 | Green |
| 2,418,907 A | 4/1947 | Schreiber |
| 2,896,618 A | 7/1959 | Schaefer |
| 3,403,681 A | 10/1968 | Hoey et al. |
| 3,559,650 A | 2/1971 | Larson |
| 3,563,241 A | 2/1971 | Evans et al. |
| 3,929,135 A * | 12/1975 | Thompson ............. 604/385.08 |
| 3,945,386 A | 3/1976 | Anczurowski et al. |

(Continued)

FOREIGN PATENT DOCUMENTS

| | | |
|---|---|---|
| DE | 35 17 640 A1 | 11/1985 |
| EP | 0 321 985 A2 | 6/1989 |
| EP | 0 214 867 B1 | 6/1991 |
| EP | 0 523 683 B1 | 1/1993 |
| EP | 0 596 532 A1 | 5/1994 |
| EP | 0 649 644 A1 | 4/1995 |
| WO | WO 91/09583 | 7/1991 |
| WO | WO 91/11163 | 8/1991 |
| WO | WO 93/06804 | 4/1993 |
| WO | WO 95/00093 | 1/1995 |
| WO | WO 96/00545 | 1/1996 |
| WO | WO 97/06765 | 5/1997 |

*Primary Examiner*—Larry I. Schwartz
*Assistant Examiner*—C. Lynne Anderson
(74) *Attorney, Agent, or Firm*—Dority & Manning

(57) ABSTRACT

Method for directed drainage of fluids emerging in a localized manner, and further absorbent article which comprises: a front region; a rear region; a central region between the front and rear regions; an upper layer permeable to body fluids and which faces the body of the user when the absorbent article is in use; a lower layer impervious to body fluids and which is remote from the body of the user when the absorbent article is in use; a fluid-distribution layer disposed between the fluid-permeable layer and the impervious layer, the fluid-distribution layer extending from the front region to the rear region; and a fluid-storage layer disposed between the lower layer and the fluid-distribution layer. The absorbent article comprises one or more transport layers transferring fluid from the fluid-distribution layer at least into the part of the fluid-storage layer located in the front and/or rear region of the absorbent article.

26 Claims, 8 Drawing Sheets

U.S. PATENT DOCUMENTS

| | | | | |
|---|---|---|---|---|
| 4,055,180 A | * | 10/1977 | Karami | 604/368 |
| 4,323,069 A | * | 4/1982 | Ahr et al. | 604/378 |
| 5,342,336 A | | 8/1994 | Meirowitz et al. | |
| 5,437,653 A | | 8/1995 | Gilman et al. | |
| H1511 H | | 12/1995 | Chappell et al. | |
| 5,527,300 A | * | 6/1996 | Sauer | 604/378 |
| 5,569,226 A | * | 10/1996 | Cohen et al. | 604/378 |
| 5,603,707 A | * | 2/1997 | Trombetta et al. | 604/383 |
| 5,788,684 A | * | 8/1998 | Abuto et al. | 604/368 |
| 5,803,920 A | * | 9/1998 | Gilman | 604/378 |
| 5,810,798 A | | 9/1998 | Finch et al. | |
| 5,961,505 A | | 10/1999 | Coe et al. | |
| 6,011,195 A | | 1/2000 | Muhs et al. | |
| 6,206,865 B1 | * | 3/2001 | Chen et al. | 604/385.01 |

* cited by examiner

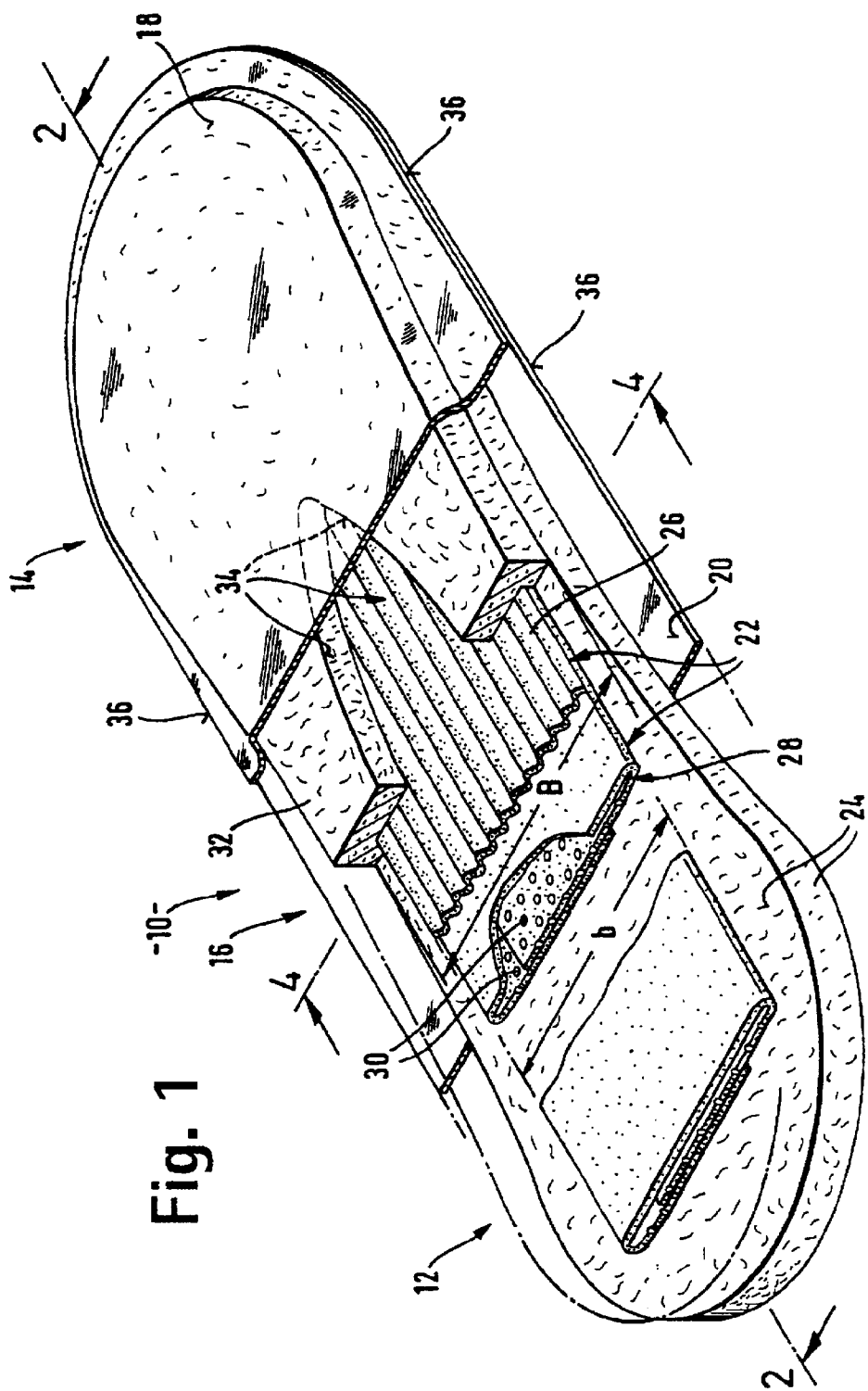

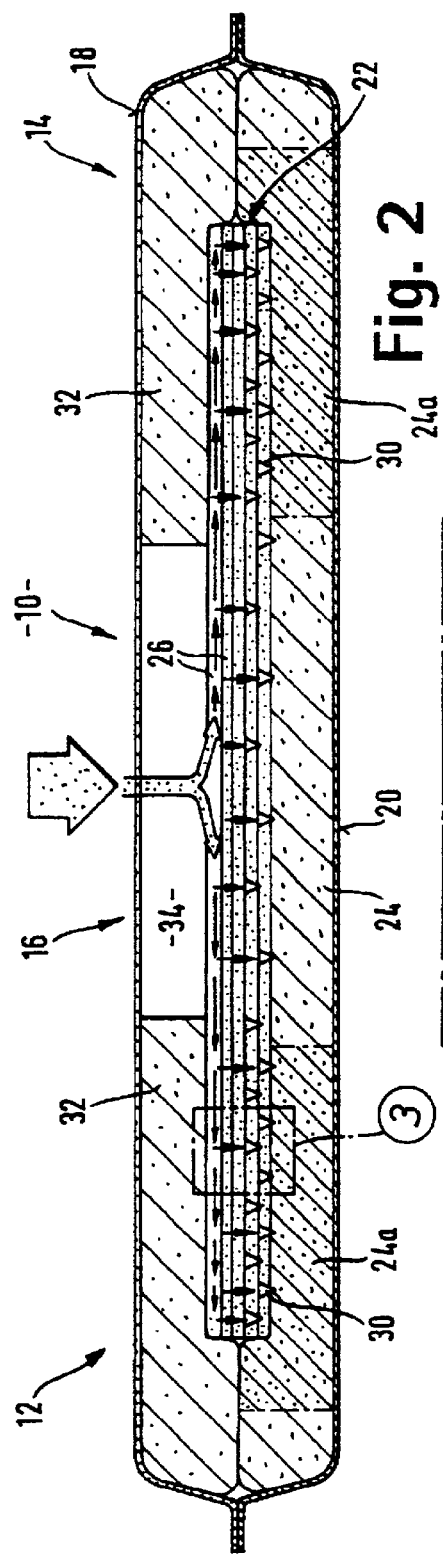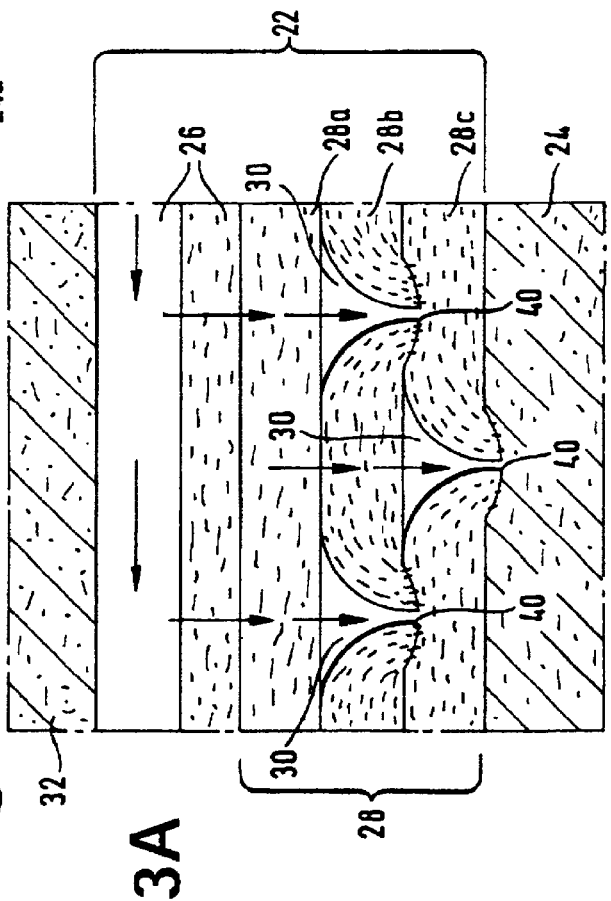

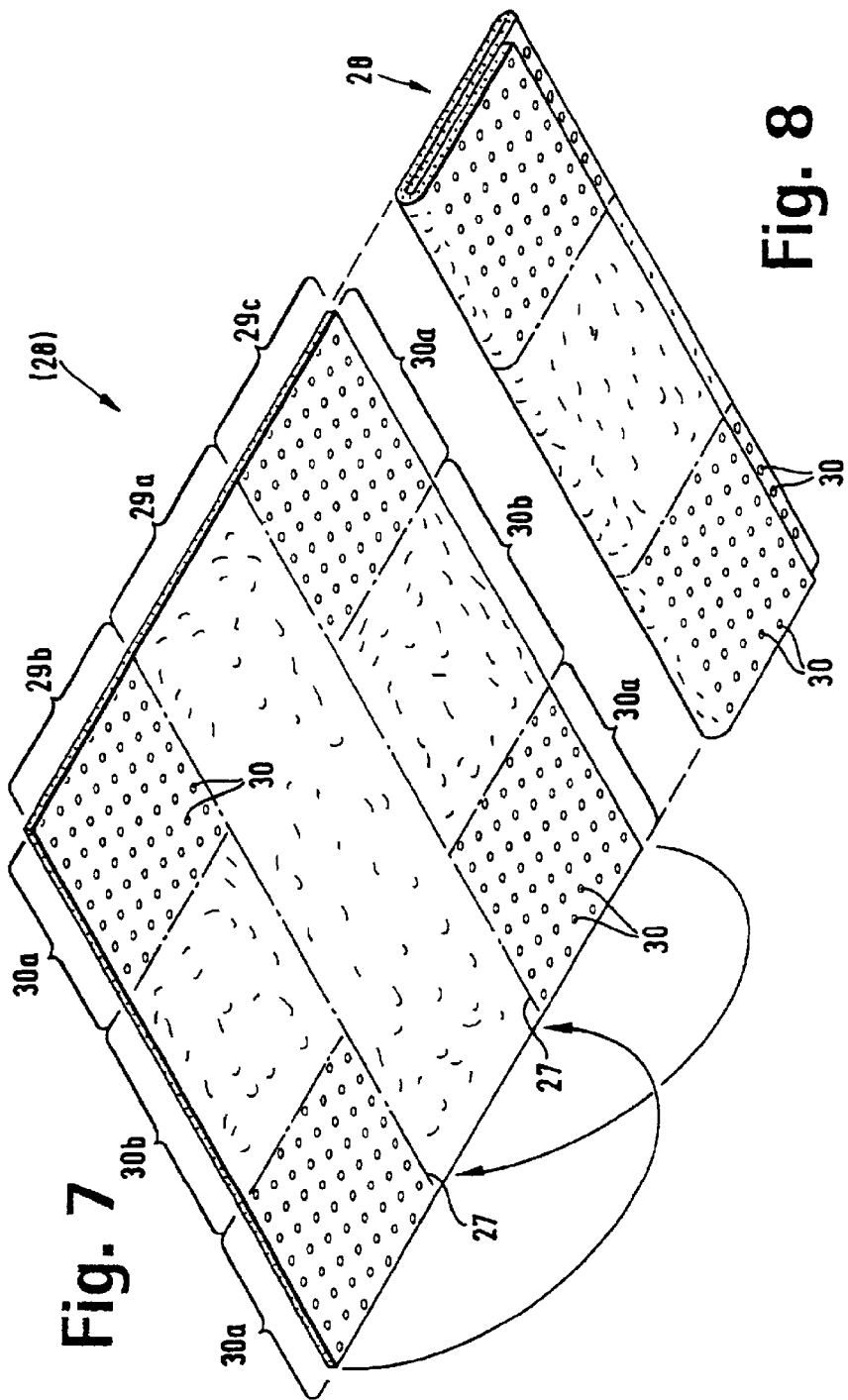

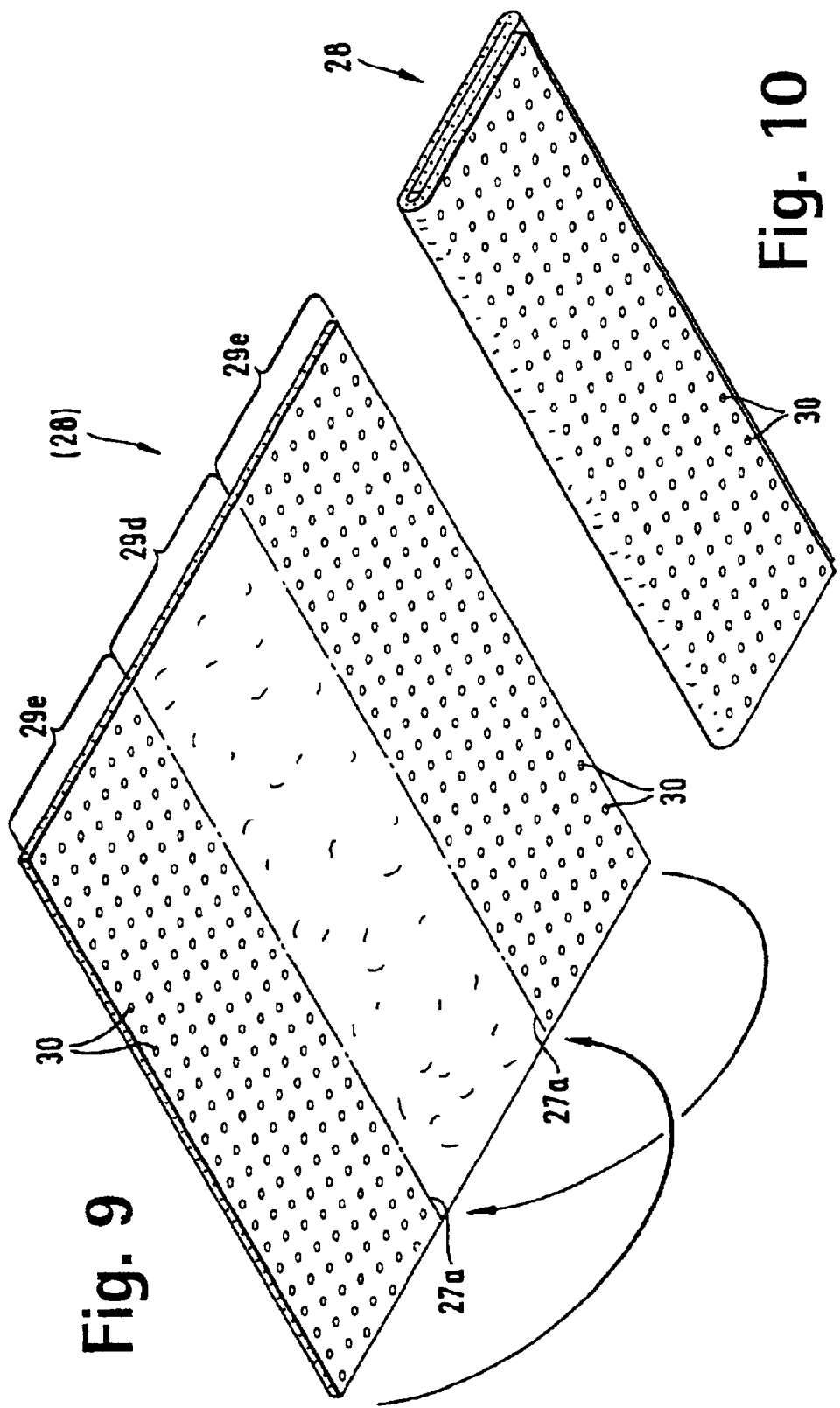

ABSORBENT ARTICLE AND PROCESS FOR THE DIRECTED DRAINAGE OF FLUIDS RELEASED IN A LOCALIZED MANNER

Cross-Reference to Related Applications

This application is a continuation of U.S. application Ser. No. 09/142,115 filed Sep. 4, 1998 now U.S. Pat. No. 6,241,714 which was the National Stage of International Application No. PCT/EP97/01144 filed Mar. 6, 1997, which claims priority to German Application No. 196 09 462.3 filed Mar. 11, 1996. Thus, U.S. application Ser. No. 09/142,115 is incorporated herein by reference in its entirety.

The present invention pertains to an absorbent article and process for the directed drainage of [bodily] fluids released in a localized manner.

Absorbent articles have been known for a long time as hygiene products. They find use, for example, as diapers, incontinence inlays, or in women's sanitary pads. These absorbent articles are constructed in such a way that they can absorb and store liquid bodily excretions such as urine, menstrual fluid, or blood. Women's sanitary pads are used, for example, to absorb the liquids excreted prior to, during and after menstruation. Women's sanitary pads are worn on the outside of the body (externally) and, in this regard, they differ from tampons, which are introduced into the female vagina and can thus be termed "internal" products.

The surface [of such a pad], which is turned toward the body, exhibits wet areas after contacting by a liquid; this is frequently found to be disadvantageous when using known absorbent articles and leads to an unpleasant feeling for the wearer. Investigations in this connection have shown that conventional women's sanitary pads cause rewetting even when one has exhausted only about 5% of the theoretical capacity of the pad to absorb liquids. In addition, the excreted bodily liquids frequently leave visible residues behind on the surface of the absorbent article used, [which] tempts the user of the article to change the absorbent article more frequently than would be necessary as a result of absorbing liquid [to the maximum extent].

The problem for the present invention is thus to provide an absorbent article and a process for the directed drainage of [bodily] liquids, released in a localized manner, whereby the absorptive capacity of the liquid storage material in the absorbent article is utilized optimally and whereby, even after extended use of the absorbent article, [only] traces of its use, which are as few as possible, are visible on the side of the absorbent article, which is turned toward the body.

The present invention solves this problem by means of the absorbent article in accordance with independent claim 1 and the process in accordance with independent claim 34. Additional advantageous embodiments of the absorbent article in accordance with the invention and of the process in accordance with the invention arise from the dependent claims, the specification, and the drawings.

The absorbent article in accordance with the invention has a front area and a rear area connected to one another by means of a central part. The layer, which is turned toward the body during use of the article, is formed from a material that is permeable to liquids whereas, in contrast, the layer of the article that is turned away from the body is a layer that is impermeable to liquids. A layer that can distribute the fluids that enter the absorbent article in a preferential direction within the article is located between the layer that is turned toward the body and that is permeable to liquids, and the layer which is turned away from the body and which is impermeable to liquids. In the following sections, this [intermediate layer] is designated as a liquid distribution layer. In addition, the absorbent article in accordance with the present invention has a layer in which the liquid that has entered is absorbed and retained (the so-called liquid storage layer, which is also termed the absorptive element). Finally, the absorbent article in accordance with the invention contains a means for transporting the fluid which has penetrated into the article from the liquid distribution layer to the liquid storage layer. As a result of the specific structure of the absorbent article in accordance with the invention, one achieves the situation in which the storage of a liquid which has penetrated [the article] takes place preferentially in the terminal areas of the article. In addition, the storage of liquid in the lower layers takes place more easily; as a result, a so-called "bottom-up-filling" effect is produced.

The liquid distribution layer is preferably arranged in such a way that the liquid which has penetrated the absorptive element is led from the impact site, which is located centrally in the central part, into the front and rear areas. In the case of an absorbent article that is constructed in an oblong manner, distribution of the liquid therefore takes place in the longitudinal direction.

In this regard, the liquid distribution layer can extend beyond the total breadth of the absorbent article or, as the case may be, the liquid storage component. However, when using an efficient liquid transport system within the absorbent article, it can be sufficient if the breadth of the liquid distribution layer is less than the least breadth of the absorbent article or, as the case may be, the liquid-storing layer.

The distribution of the liquid, i.e., drainage, to the front rear ends of the article is achieved especially favorably by way of the feature that the liquid distribution layer has an undulating strip of material or a pleated strip of material whose undulations are arranged in such a way that the liquid is preferentially drained off in the longitudinal direction and toward the ends of the article. The undulating strip of material or the pleated strip of material can consist of a textile material, for example, whereby this has virtually no absorptive capacity of its own; as a result, one prevents the situation in which this strip of material permanently retains the liquid. The undulating strip of material serves primarily in draining off the liquid ,i.e. drainage, and as a spacer. Visible discernment of the absorptive element, which has been in contact with liquid, can be prevented if the undulating strip of material additionally contains a colorant such as a dye; as a result, one increases the subjective feeling of cleanness of the male or female wearer of the article.

The undulating strip of material is preferably connected to an additional strip of material that, on the one hand, can assist in stabilizing the undulations and, on the other hand, can also assist the directed transport of the liquid that has penetrated into the article. A so-called uncreped-through-air-dried material, UCTAD material, has proven to be especially suitable for such an additional strip of material.

A preferred UCTAD material contains at least 10 wt % of high-yield pulp [cellulose] fibers based on the weight of the dry substance, with a wet strength agent being added to it in such a quantity that the ratio of the wet tensile strength to the dry tensile strength amounts to approximately 0.1. High-yield pulp fibers contain a large amount of lignin, to which the [high] elasticity of the fibers in the wet state can be attributed. The resin bonds, formed by the wet strength agent, immobilize the wet elastic fibers into a sheet-like structure that adapts itself to the structure of the strip of material on which drying (through-drying) takes place. The bonds formed by the wet strength agent are hardened to completion during the drying process; in this way, bonds that are resistant to moisture are formed in turn, this generates the highly elastic properties of an appropriate strip of material in the wet state. This property is maintained by the strip of material since a creep-generating step or another other step, which could destroy the bonds, is not carried out in the case of an UCTAD process. Thus, the UCTAD material is superbly well suited for transporting liquids since the material is also stabilized in the wet state.

Another form of embodiment of the liquid distribution layer in the absorbent article in accordance with the invention is configured in such a way that the undulating strip of material is pleated on a supporting material that is permeable to liquids and that extends over the entire breadth of the absorbent article, whereby the undulating strip of material needs to occupy only part of the total breadth of the supporting material. The additional strip of material can again be arranged underneath the undulating strip of material with the support. The aforementioned materials, i.e., a spun textile material or UCTAD are suitable for the undulating strip of material or the additional strip of material. Spun textile material is also suitable as the supporting material.

Other important elements of the absorbent article in accordance with the invention include a means for transferring the fluid from the liquid distribution layer at least into that part of the liquid storage layer located in the front area and/or the rear area of the absorbent article. These means can, for example, be areas in the liquid distribution layer that are brought into close contact with the liquid storage layer via compression, e.g., using a calendaring process. These areas, which have been brought into contact with one another via compression, are preferably arranged in a point-like manner.

The transport of liquid from the liquid distribution layer into the liquid storage layer can also be assisted by joining the two designated layers by means of an adhesive. An adhesive that is hydrophilic has proven to be especially favorable. The connection of the liquid distribution layer to the liquid storage layer by means of the adhesive preferably occurs in a point-like manner. Geometrical patterns are also preferred, whereby a diamond-shaped pattern allows an especially effective transfer of the liquid from the liquid distribution layer to the liquid storage layer.

In accordance with another preferred form of embodiment of the absorbent article in accordance with the invention, the means for transferring the fluid from the liquid distribution layer to the liquid storage layer are arranged in such a way that the liquid distribution layer has funnel-shaped openings aligned in such a way that the funnel-shaped openings taper in the direction of the liquid storage layer. Directed draining away of liquid from the liquid distribution layer to the liquid storage layer is ensured by these funnel-shaped openings. In addition, the funnel-shaped openings keep the liquid distribution layer at a certain distance from the liquid storage layer; as a result, one effectively prevents any retransport of liquid from the liquid storage layer back to the liquid distribution layer. In this regard, the funnel-shaped openings are preferably located in the additional strip of material connected to the pleated strip of material.

According to a preferred form of embodiment of the article in accordance with the invention, the additional strip of material has a central area, as seen in the longitudinal direction, without funnel-shaped openings and the undulating strip of material is applied to the central area. The funnel-shaped openings are located in the area located at the edges as seen in the longitudinal direction. The edges with the funnel-shaped openings are now folded under the area provided with the undulating strip of material, in such a way that the funnel-shaped openings with their tapering areas lie opposite the liquid storage layer. As a result of introducing the funnel-shaped openings into the additional strip of material after fabrication of such additional strip of material, e.g., by piercing with needles or other suitable mechanical means, the additional strip of material becomes perforated; as a result, small absorptive feet can form at the tapering end of the funnel-shaped openings. Especially effective fluid transport is achieved when these small absorptive feet are in contact with the liquid storage layer since this assists the directed transport of liquid from the liquid distribution layer to the liquid storage layer. The folding inward of the additional strip of material can be arranged in such a way that it takes place from each side as far as, approximately, the middle of the additional strip of material. However, the edge areas can also have the same breadth as the area with the additional strip of material on which the undulating strip of material has been pleated. As a result of folding in the edge areas, which have been provided with funnel-shaped openings, a triple layer structure is formed underneath the additional strip of material. This triple layer structure effectively prevents rewetting from arising in the liquid distribution layer by liquid from the liquid storage (component).

Directed transport of liquid from the liquid distribution layer to the liquid storage layer or absorptive elements is also assisted by the fact that the liquid storage layer has areas with a higher liquid retention capacity, whereby liquid is preferentially released to these areas. If the liquid storage layer is assembled from cellulose, a higher retention capacity can be produced by compacting the cellulose material. As a result of compaction, the pores or, as the case may be, the pore sizes, in the cellulose material are reduced, which increases the capillary forces. Another possibility for forming locally limited areas with a higher liquid retention capacity in the absorptive elements comprises the use of superabsorbent materials in these locally limited areas.

If, as in the present case, one desires optimum utilization of the absorptive elements for the storage of liquids, it is an advantage if the terminal areas of the absorbent article initially store the liquid and that the storage of liquid takes place in the central part of the [absorbent] article only when the absorptive capacities of the terminal areas have become exhausted. By doing this, one can optimally utilize the capacity of the absorptive elements; as a result, the male or female wearer of the absorbent article does not have to change it as frequently.

This directed filling up of the absorptive element with liquid can also be assisted by way of the feature that the additional strip of material in the central part of the absorbent article does not have any funnel-shaped openings, with the funnel-shaped openings being arranged only in the front area and/or in the rear area of the absorbent article. While impacting the absorbent article [by liquid] in the central part, one thereby prevents the liquid which enters the article from becoming stored directly in the area of the liquid storage layer that lies underneath the entrance area. This is less desirable since the absorptive capacity of the absorbent article cannot be fully exhausted before rewetting takes place on the surface of the article turned toward the body.

The danger of rewetting can also be minimized by arranging a barrier layer, which is impermeable to liquids, between the lateral edges of the absorbent article and the liquid distribution layer. This is especially recommended when the breadth b of the liquid distribution layer is less than the least breadth B of the liquid storage layer. This barrier layer brings about the situation in which the liquid, released from the liquid storage layer, cannot get past the liquid distribution layer and onto the surface of the absorbent article; as a result, one further increases the level of comfort of wearing the absorbent article.

In addition, the absorbent article in accordance with the invention can contain a liquid-absorbing layer between the layer that is permeable to liquids and the liquid distribution layer. This liquid-absorbing layer is not provided, in the first instance, to serve as the primary storage component or as a secondary storage component. On the contrary, the purpose of the liquid-absorbing layer is to be seen in the feature that liquid released from the liquid storage layer, or, as the case may be, liquid that could not even enter the liquid storage layer in the first place, is intercepted on the surface of the absorbent article prior to its release. Thus the layer that absorbs liquids is to be regarded as a storage device that, in the case of an excessive demand on the liquid storage layer, is capable of taking up and storing liquids before these lead to re-wetting of the surface of the absorbent article. In order to not unnecessarily hinder the penetration of liquids into the absorptive elements and the distribution of the liquid via the liquid distribution layer, it is preferable if the liquid-absorbing layer has a centrally located opening that passes right through the entire layer. This opening should he arranged in such a way that, when wearing the absorbent article, it lies opposite the bodily opening from which the liquid to-be-absorbed will be released. The layer that absorbs liquids can be assembled from a cellulose material or it can contain such a cellulose material. A layer that comprises a cellulose material is soft and therefore increases the level of comfort when wearing an appropriately assembled absorbent article.

Another suitable material for the layer that absorbs liquids is a cellulose mixture such as a so-called coform material. A coform material consists of cellulose fibers and polypropylene fibers in the most widely differing mixing ratios. The polypropylene fibers are extruded. The layer that absorbs liquids and the layer stores liquids can consist of the same material.

The barrier layer, which is impermeable to liquids, and the liquid-impermeable covering layer of the absorbent article in accordance with the invention, can be manufactured from polyethylene, polypropylene, or mixtures of these polymers. In order to ensure snug positioning and to prevent slippage when wearing the absorbent article, an adhesive layer can be applied to the outside of the liquid-impermeable covering layer, whereby the absorbent article can be fastened inside an item of clothing by means of the adhesive layer.

The directed transport of liquid in the absorbent article in accordance with the invention can also be assisted by additional means such as additional strips of material with a preferential direction for transporting [liquids]. Such an additional means is advantageously arranged between the liquid distribution layer and the liquid storage layer.

The liquid-permeable covering layer and the layer that absorbs liquids can be joined to one another with ease, e.g., by compression at discrete points.

The absorbent article in accordance with the invention can find use, in particular, as a woman's sanitary pad or a woman's hygiene inlay.

In addition, the present invention provides a process for the directed drainage of [bodily] liquids released in a localized manner. In this connection, an absorbent article is in contact with a liquid and the liquid enters the absorbent article via a liquid-permeable covering layer. The liquid entering is then transferred, by means of a liquid distribution layer, to the areas of the absorbent article in which liquid storage is desired. The transfer of liquid from the liquid distribution layer to the liquid storage layer takes place by means that permit the directed transport of the liquid. It is especially preferred if, in order to carry out the process in accordance with the invention, use is made of an absorbent article in accordance with the invention.

The present invention will be elucidated in more detail below on the basis of the drawings and the preferred forms of embodiment. The following aspects are shown in the drawings:

FIG. 1 shows a perspective view of a form of embodiment of the article in accordance with the invention, whereby the article is partially in sectional form;

FIG. 2 shows a functional longitudinal section through the absorbent article in accordance with the invention along the line 2—2 in FIG. 1;

FIG. 3A shows an enlarged section of an area from FIG. 2;

FIG. 7 shows an illustration, in detail, of part of the liquid distribution layer in a form of embodiment of the absorbent article in accordance with the invention;

FIG. 8 shows the part of the liquid distribution layer which is shown in FIG. 7 in the form in which it is folded together and ready for use;

FIG. 9 shows a detailed illustration of part of a liquid distribution layer in another form of embodiment of the absorbent article in accordance with the invention;

FIG. 10 shows the part of the liquid distribution layer which is shown in FIG. 9 in the form in which it is folded together and ready for use.

Figure 4:
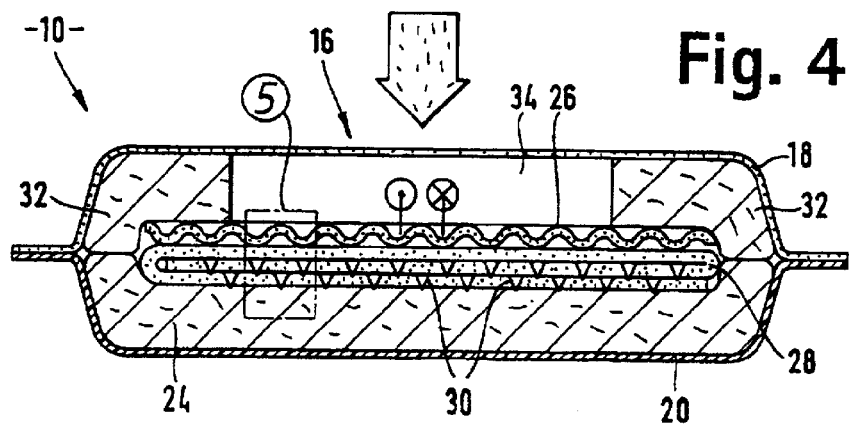
FIG. 4 shows a cross section along the line 4—4 in FIG. 1 through the form of embodiment of the absorbent article shown in FIG. 1.
Figure 5:
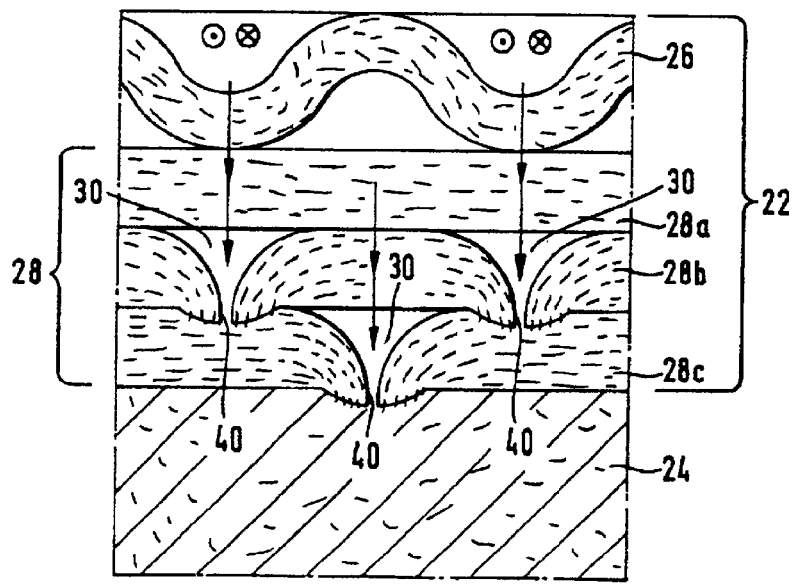
FIG. 5 shows a section, which is shown on an enlarged scale, of an area from FIG. 4.

FIG. 1 shows an absorbent article 10 with a front area 12, a rear area 14, and a central part 16 that joins the front and rear areas together. The liquid-permeable, upper covering layer of highly pigmented spun textile material is given the reference number 18 and the lower liquid-impermeable layer of the absorbent article is given the reference number 20. The liquid distribution layer 22 is arranged below the liquid-permeable layer 18. In the form of embodiment in accordance with FIG. 1, the directed transport of liquids into the terminal areas of the absorbent article 10 takes place by means of the undulating strip of material 26. As illustrated in FIGS. 1, 4, and 5, the transverse undulated configuration of the undulating strip defines longitudinal transport channels that, in some embodiments, may be void of any tangible material which would impede free flow of liquid along the channels. The undulating strip of material 26 is pleated onto an additional strip of material 28. The undulating strip of material 26 is assembled from a textile material (pigmented spun textile material) and the additional strip of material 28 is assembled from an UCTAD material. In this regard, the additional strip of material 28 is folded over downward in the edges so that the areas that have been folded over come to lie parallel to the undulating strip of material. Passages defining funnel-shaped openings 30 are to be found in the folded over areas at the additional strip of material 28. The liquid storage layer 24 is located underneath the additional strip of material 28.

According to another preferred form of embodiment of the absorbent article in accordance with the invention, this can contain a layer 32 that absorbs liquids. This layer 32 that absorbs liquids is intended to intercept liquid which has been taken up in the liquid storage component 24 and which is released again from this, and passes by the liquid distribution layer 22 laterally before this [liquid] can be released on the surface of the absorbent article via the liquid-permeable layer 18. It is especially favorable if the layer 32 that absorbs liquids has a centrally located opening 34 that passes right through it. During use of the absorbent article, the central opening 34 comes to lie opposite the male or female wearer's bodily opening from which the liquid which is to be absorbed is released. The opening 34 ensures that the liquid that is to be absorbed does not have to pass through an absorbent material before this [liquid] arrives in the liquid distribution layer 22, with the desired distribution of the liquid in the longitudinal direction of the absorbent element being assisted in this way. The liquid-permeable strip of material 18 and the undulating strip of material 26 are manufactured from a textile material that contains pigments. As a result, liquid that is retained in the liquid storage layer 24 cannot be visibly discerned as far out as the surface of the absorbent article. This increases the user's acceptance of the absorbent article. Even after contacting the absorbent article with liquid, one can scarcely see, from the outside, that this has already taken up large quantities of liquids under certain circumstances.

FIG. 2 is a functional longitudinal section along the line 2 in FIG. 1 and through the absorbent article in accordance with the invention. In this regard, the arrows indicate the direction of flow of liquid within the absorbent article. The liquid, which passes through the liquid-permeable layer 18, impinges on the liquid distribution layer 22. In this way, the liquid distribution layer 22 prevents the liquid from passing directly through to the layer 24 that absorbs liquids. Rather, directed transport takes place toward the front area 12 or the rear area 14 of the absorbent article. The transfer of liquid from the liquid distribution layer 22 to the layer 24 that absorbs liquids preferentially takes place in this way to the areas of increased liquid retention capacity 24*a* of the liquid storage layer 24. The storage layer 24 comprises cellulose. The increased liquid retention capacity of the areas 24*a* is achieved by compressing the cellulose material, whereby this is represented by the denser shading in FIG. 2. The funnel-shaped openings 30, arranged in the layer 22, are also illustrated; these bring about vertical transport of the liquid from above to below, whereby—because of the structure of the funnel-shaped openings—virtually no transport of the liquid from deeper areas takes place back into higher areas. FIG. 2 also shows the layer 32 that absorbs or intercepts any liquid not absorbed in the liquid storage component 24 before this can be released again through the liquid-permeable layer 18 and onto the surface of the absorbent article.

Figure 3B:
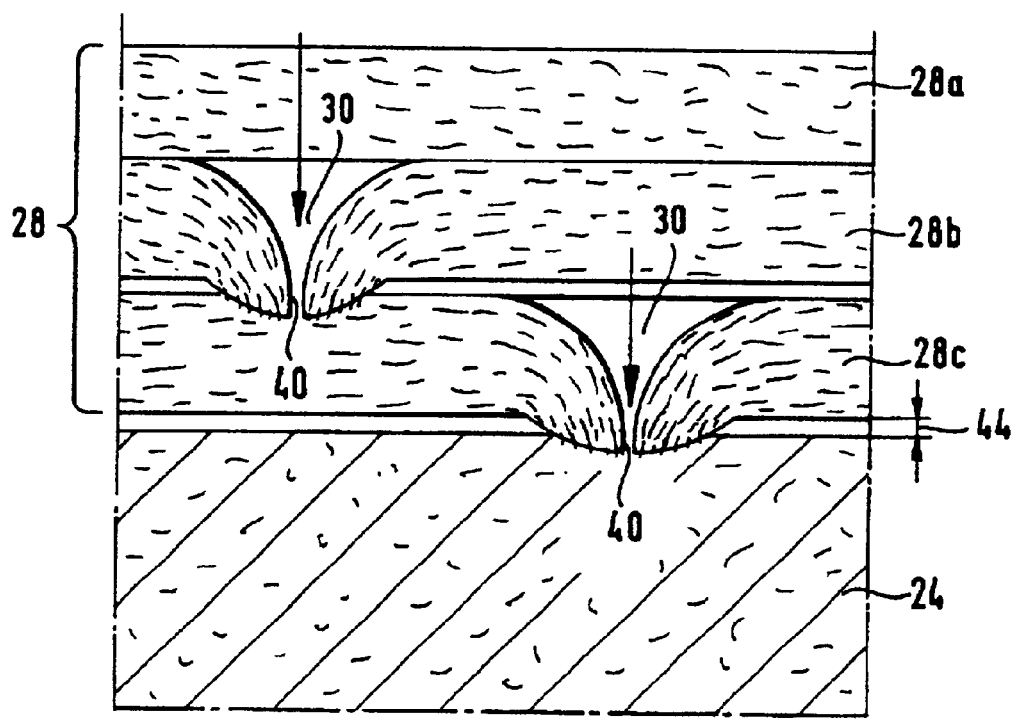
FIG. 3B shows an enlarged section of an area from FIG. 2 according to another form of embodiment in accordance with the invention.

FIG. 3A is an enlarged section of the contact area between the liquid distribution layer 22 and the liquid storage layer 24. The preferential direction of liquid transport is again indicated by the arrows in FIG. 3. FIG. 3 shows the additional strip of material 28 assembled in the form of three layers. In this regard, the uppermost layer 28*a*, to which the undulating strip of material is applied, is arranged without funnel-shaped openings. In contrast, the take-away layers 28*b* and 28*c*, which lie underneath, have funnel-shaped openings 30. As a result of the configuration of the funnel-shaped openings 30, one brings about the situation in which the take-away layers 28*b* and 28*c* can be separated from one another by a certain distance as shown in FIG. 3B; as a result, one prevents any upward return of liquid. A separation 44 can be formed (FIG. 3B) between the take-away layer 28*c* and the additional strip of liquid storage layer 24 by means of the funnel-shaped openings 30, whereby this separation also contributes to the prevention of liquid being transferred back from the liquid storage layer 24 to the liquid distribution layer 28.

The small absorptive feet 40 at the outlet of the funnel openings 30 are also shown in FIGS. 3A and 3B. The small absorptive feet 40 are each fastened to the strip of material that lies below them and, in this way, they assist the directed transport of liquid into the liquid storage layer 24.

FIG. 4 shows a cross section along the line 4—4 in FIG. 1 through an absorbent article in accordance with the invention. The arrow shows the direction of entrance of the liquid into the absorbent article. The liquid that has entered is then transported along the undulating strip of material 26, which leads to the ends of the absorbent article 10. Furthermore, FIG. 4 shows the additional strip of material 28 in the form of a cross section. The part of the strip of material 28, which supports the undulating strip of material 26, does not contain any openings. The lateral parts, which are arranged underneath, are each in fluid contact with the layer located underneath, via the openings 30. Furthermore, the funnel-shaped openings 30 extend through the lowermost area of the layer 28 to the liquid storage layer 24.

FIG. 5 is a section, which is illustrated on an enlarged scale, from FIG. 4. It also shows the undulating strip of material 26 in the form of a cross section. The undulating strip of material 26 is connected to the additional strip of material 28 via a number of points of contact. The layer 28 comprises the three layers 28*a*, 28*b*, and 28*c*. The layer 28*a*, which supports the undulating strip of material 26, does not have any openings 30. In contrast, the two take-away layers 28*b* and 28*c*, which are arranged below it, contain funnel-shaped openings 30 that assist the vertically directed flow of that which has penetrated therein. A canal-type structure is generated by this flow, which is directed vertically downward, and prevents any upward return of liquid. Upward release of liquid via the layer 28 almost never takes place.

Figure 6:
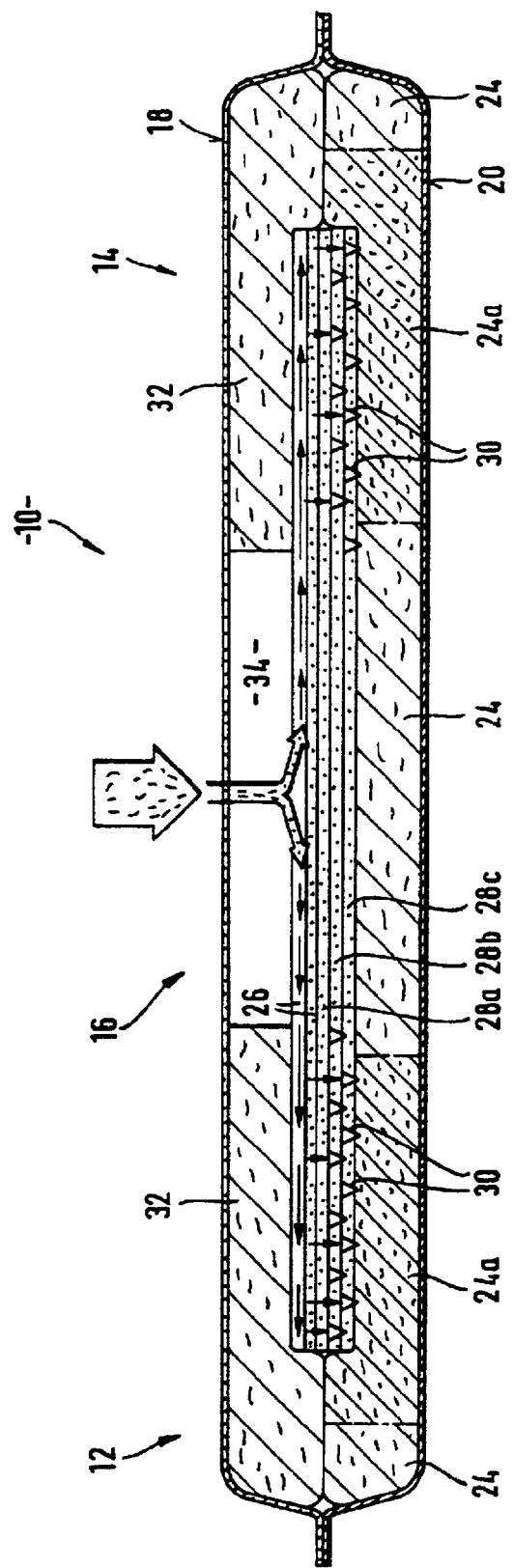
FIG. 6 shows a functional longitudinal section through another form of embodiment of the absorbent article in accordance with the invention.

FIG. 6 shows a functional longitudinal section through another form of embodiment of the absorbent article in accordance with the invention. The form of embodiment in accordance with FIG. 6 exhibits the special feature that the additional strip of material 28 does not contain funnel-shaped openings 30 in the central area of the absorbent article. As a result, one achieves the situation in which the transport of liquid becomes even more effective in the terminal areas of the strip of material 28, which are located on the long sides, before the liquid is released to the liquid storage layer 24 or 24*a*.

FIG. 7 shows the additional strip of material 28. Seen in the longitudinal direction, this has a central zone 29*a* that is free of funnel openings. Sections 29*b* and 29*c* of the additional strip of material 28, which are located at the edges, contain areas 30*a* with openings and, in addition, an area 30b without openings. When using the additional strip of material 28 in the absorbent article 10 in accordance with the invention, this strip of material 28 is folded over toward the inside along the lines 27; as a result, one obtains the structure shown in FIG. 8. The folded structure of the strip of material 28 now contains selective openings 30 in the terminal areas as seen in the longitudinal direction, whereas the central part is completely free of openings. As a result of this construction of the additional strip of material 28, one produces a directed flow of liquid, which has penetrated into the absorbent article, in the front and rear parts of the absorbent article, whereby this directed flow has already been described above in further detail. The area of the liquid storage layer 24, located in the central part of the [absorbent] article, also becomes filled with liquid, but only when the liquid storage layer in the front and rear terminal areas of the absorbent article have become full by absorbing liquid.

FIG. 9 shows another form of embodiment of the additional strip of material 28. Seen in the longitudinal direction, this also has a central zone 29d that is free of funnel openings. In contrast, the sections 28c, located at the edges, are provided with openings 30 that pass right through them. Before the additional strip of material can find use in the absorbent article in accordance with the invention, it is folded along the lines 27a; as a result, one obtains the structure shown in FIG. 10. The pleated strip of material can be applied to the area 29d and the strip of material 28 can be incorporated into the article with the funnel-shaped openings 30 pointing downward.

Figure 11:
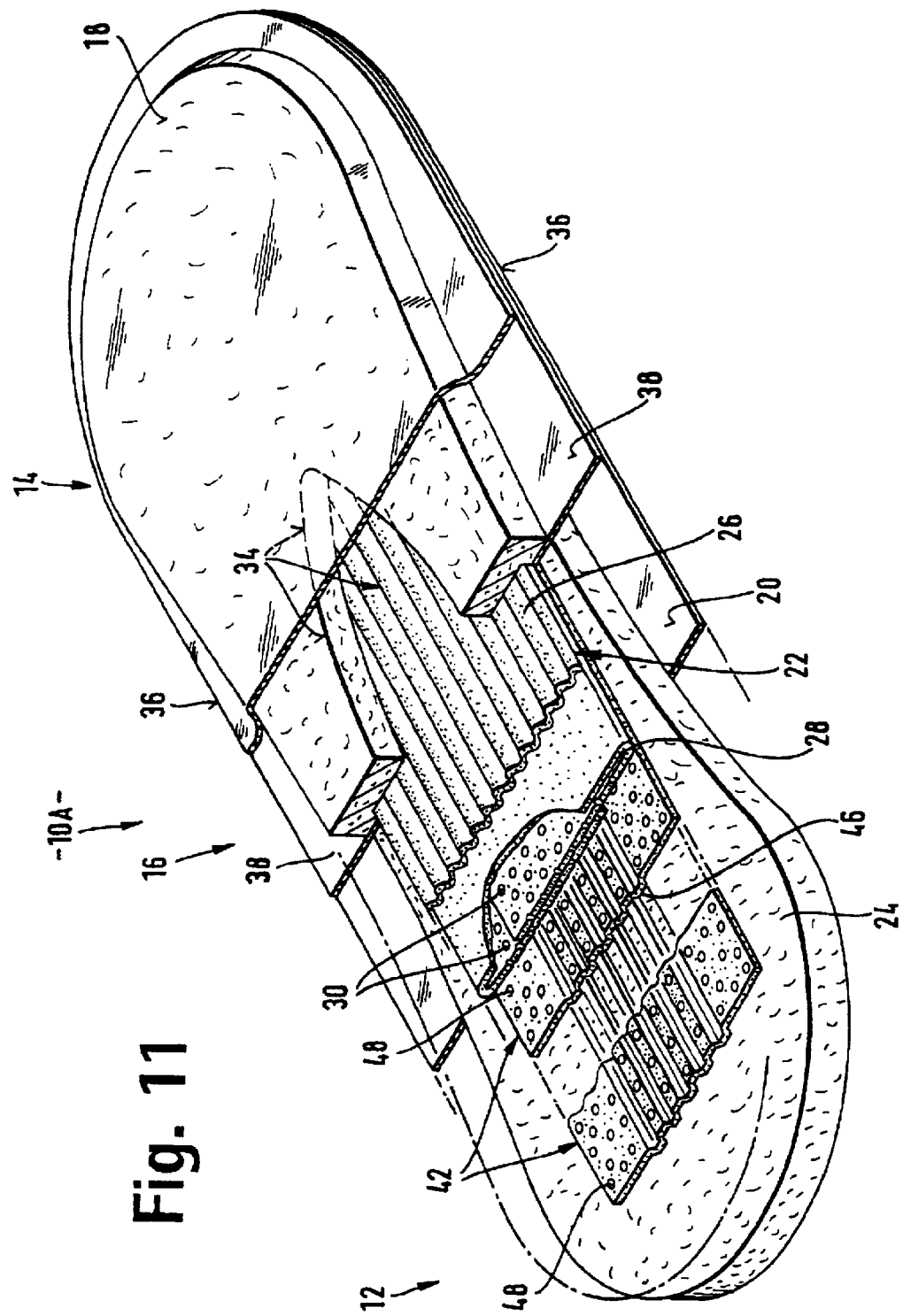
FIG. 11 shows a perspective view of another form of embodiment of an absorbent article in accordance with the invention.

Finally, FIG. 11 shows another preferred form of embodiment of the absorbent article in accordance with the invention. The form of embodiment 10A in accordance with FIG. 11 contains the essentially liquid-impermeable or semipermeable barrier layer 38 as another safeguard against flowback. This prevents the situation in which liquid, which is released from the liquid storage layer 24, can enter the liquid-absorbing layer 32 and thence onto the surface of the absorbent article, possibly via the liquid-permeable layer 18. In this regard, the barrier layer 38 extends from the edge 16 up to the liquid distribution layer 22. The layer 38 can be an integral component or extension of the liquid-impermeable layer 20 and can therefore consist of the same material as the layer 20. Another material, which is suitable for the barrier layer 38, is poly(ethylene oxide), which provides a semipermeable membrane. This can be inserted, in the form of a layer, between the liquid-permeable layer 18 and the liquid-impermeable layer 20. The incorporation of an impermeable or semipermeable barrier layer is always an option when the breadth b of the liquid distribution layer is less than the least breadth B of the liquid storage layer 24 (see FIG. 1).

Furthermore, the absorbent article 10A, shown in FIG. 11, contains an additional strip of material 42 that further assists the longitudinally directed distribution of liquid within the absorbent article. Like the layer 28, the layer 42 is also manufactured from an UCTAD material. The strip of material 42 has grooves 46 that extend along the longitudinal direction and assist the distribution of liquid in the desired longitudinal direction of the [absorbent] article. In addition, the layer 42 has funnel-shaped openings 48 through which the liquid can be transferred to the liquid storage component 24.

What is claimed is:

1. An absorbent article having a length and a width, a front area and a rear area, and a central area between the front and rear areas, said absorbent article comprising:
    (a) a liquid-permeable layer, which, when the absorbent article is in use, is turned toward a body of a wearer;
    (b) a liquid-impermeable layer, which, when the absorbent article is in use, is turned away from such body of such wearer;
    (c) a liquid distribution layer disposed between said liquid-permeable layer and said liquid-impermeable layer, said liquid distribution layer comprising
        (i) an undulating strip of material (26) from the central area into at least one of the front area and the rear area, and
        (ii) an additional strip of material (28) disposed between the undulating strip of material (26) and the liquid-impermeable layer, and extending between the front area and the rear area, said additional strip of material (28) having openings formed therethrough exclusively in one or both of the front area and the rear area of the absorbent article such that said formed openings are spaced from each other by the central area of the absorbent article which is devoid of such formed openings; and
    (d) a liquid storage layer between the liquid-impermeable layer and the liquid distribution layer, said liquid distribution layer transferring fluid to the liquid storage layer in one or both the front area and the rear area, said undulating layer comprising elongate undulations defining elongate open flow channels between said undulating layer and underlying and overlying elements of said absorbent article which are in contact with said undulating layer.

2. An absorbent article as in claim 1, said openings in said additional strip of sheet material reflecting having been mechanically-formed subsequent to formation of said additional strip of sheet material.

3. An absorbent article as in claim 1 wherein the undulating strip of material selectively facilitates transfer of fluid longitudinally, along the length of said absorbent article, into one or both the front area and the rear area of the absorbent article.

4. An absorbent article as in claim 1, the undulations being arranged so as to form elongate and generally continuous transport channels extending along the length of said absorbent article.

5. An absorbent article as in claim 1 wherein the undulating strip of material defines elongate undulations therein, connected at spaced locations to said additional strip of material.

6. An absorbent article as in claim 1 wherein said additional strip of material (28) comprises an uncreped through-air-dried material.

7. An absorbent article as in claim 4, said liquid storage layer extending from the central area into the front area and the rear area, the liquid storage layer having a higher liquid retention capacity per unit area of said absorbent article in the respective one or both of the front area or the rear area than in the central area.

8. An absorbent article as in claim 1, said liquid distribution layer transferring fluid to at least part of the liquid storage layer at areas of the liquid distribution layer and of the liquid storage layer, which are brought into contact with one another via compression.

9. An absorbent article as in claim 1, the liquid distribution layer comprising fibrous compositions about said openings, wherein the openings in the liquid distribution layer have discharge ends at a major surface of said liquid storage layer, for transferring fluid, such funnel-shaped openings tapering inwardly tow d the liquid storage layer.

10. An absorbent article having a length and a width, a front area and a rear area, and a central area between the front and rear areas, said absorbent article comprising:
    (a) a liquid-permeable layer which, when the absorbent article is in use, is disposed toward a body of a user;
    (b) a liquid-impermeable layer which, when the absorbent article is in use, is disposed away from such body of such user;

(c) a liquid distribution layer comprising an uppermost layer and at least one take-away layer, at least one of said at least one take away layer having discrete passages therethrough, and zones of relatively greater fiber density adjacent the discrete passages, the relatively greater fiber density promoting movement of liquid toward the liquid-impermeable layer, the discrete passages being disposed exclusively in one or both of the front area and the rear area of the absorbent article whereby the central area is devoid of the discrete passages, said uppermost layer being positioned between said liquid-permeable layer-and said at least one take-away layer, and being devoid of such passages therethrough, said liquid distribution layer being disposed between the liquid-permeable layer and the liquid-impermeable layer; and (d) a liquid storage layer disposed between the liquid-impermeable layer and the liquid distribution layer, said liquid distribution layer transferring fluid to at least part of the liquid storage layer of the absorbent article.

11. An absorbent article as in claim 10, the liquid storage layer extending from the front area to the rear area of said absorbent article, the liquid storage layer having a higher liquid retention capacity per unit area of said absorbent article in the respective at least one of the front area and the rear area of the absorbent article, than in the central area.

12. An absorbent article as in claim 10 wherein areas of the liquid distribution layer and areas of the liquid storage layer are in contact with one another via compression, thereby facilitating transfer of liquid.

13. An absorbent article as in claim 10 wherein the liquid distribution layer has feet at tapering ends of the passage, said feet being in contact with the liquid storage layer at a surface of the liquid storage layer.

14. An absorbent article as in claim 10 wherein the absorbent article comprises a woman's sanitary pad or a woman's hygiene inlay.

15. An absorbent article, comprising:
(a) a liquid-permeable layer which, when the absorbent article is in use, is disposed toward a body of a user;
(b) a liquid-impermeable layer which, when the absorbent article is in use, is disposed away from such body of such user;
(c) a liquid distribution layer, which comprises discrete passages therethrough, said discrete passages facilitating movement of liquid toward the liquid-impermeable layer; and
(d) a liquid storage layer disposed between the liquid-impermeable layer and the liquid distribution layer, said liquid distribution layer comprising an overlying strip of material and an additional strip of material, said passages being arranged in edges of the additional strip of material, said edges being folded inward such that said edges are facing the overlying strip of material.

16. An absorbent article as in claim 15 wherein said edges run in a longitudinal direction of the absorbent article, and are folded over a central portion of the additional strip of material such that the passages taper inwardly toward the liquid storage layer.

17. An absorbent article as in claim 15, further comprising undulations in said overlying strip of material defining fluid transport channels extending in a longitudinal direction of said absorbent article.

18. An absorbent article as in claim 15 wherein the additional strip of material comprises an uncreped through-air-dried material.

19. An absorbent article as in claim 15 wherein the overlying strip of material contains a colorant.

20. An absorbent article having a front area, a rear area, and a central area between the front area and the rear area, said absorbent article comprising:
(a) a liquid-permeable layer which, when the absorbent article is in use, is disposed toward a body of a wearer;
(b) a liquid-impermeable layer which, when the absorbent article is in use, is disposed away from such body of such wearer;
(c) a fibrous liquid distribution layer, which promotes movement of liquid toward the liquid-impermeable layer, said liquid distribution layer being disposed between the liquid-permeable layer and the liquid-impermeable layer; and
(d) a liquid storage layer disposed between the liquid-impermeable layer and the liquid distribution layer,
said liquid distribution layer comprising areas having passages defining openings for transferring liquid, said liquid distribution layer comprising feet at ends of such passages, said feet contacting the liquid storage layer, and forming areas, between the feet, of separation between the liquid distribution layer and the liquid storage layer where the liquid distribution layer and the liquid storage layer are spaced from each other, whereby said areas of separation attenuate reverse wicking of liquid from the liquid storage layer to the liquid distribution layer.

21. An absorbent article having a front area, a rear area, and a central area arranged between the front area and the rear area, said absorbent article comprising:
(a) a liquid-permeable layer which, when the absorbent article is in use, is disposed toward a body of a wearer;
(b) a liquid-impermeable layer which, when the absorbent article is in use, is disposed away from such body of such wearer;
(c) a liquid distribution layer disposed between the liquid-permeable layer and the liquid-impermeable layer, said liquid distribution layer including at least first and second take-away layers each having funnel-shaped openings defining discrete passages, the discrete passages being disposed exclusively in one or both of the front area and the rear area of the absorbent article whereby the central area is devoid of the discrete passages, respective openings of said first take-away layer and said second take-away layer being spaced laterally from each other, with layer-to-layer surface interface between a said opening on said first take-away layer and any said opening on said second take-away layer; and
(d) a liquid storage layer disposed between the liquid-impermeable layer and the liquid distribution layer.

22. An absorbent article having a front area, a rear area, and a central area arranged between the front area and the rear area, said absorbent article comprising:
(a) a liquid-permeable layer which, when the absorbent article is in use, is disposed toward a body of a wearer;
(b) a liquid-impermeable layer which, when the absorbent article is in use, is disposed away from such body of such wearer;
(c) a liquid distribution layer disposed between the liquid-permeable layer and the liquid-impermeable layer, said liquid distribution layer including at least first and second take-away layers each having funnel-shaped openings defining discrete passages;
(d) a liquid storage layer disposed between the liquid-impermeable layer and the liquid distribution layer, wherein respective openings of said first take-away layer are spaced laterally from each other, with layerto-layer surface interface between a said opening on said first take-away layer and any said opening on said second take-away layer; and (e) said liquid distribution layer further comprising an uppermost layer disposed between the liquid-permeable layer and said take-away layers, said uppermost layer being void of any funnel-shaped openings.

23. An absorbent article as in claim 22, liquid distribution layer further comprising an undulating strip of material disposed between the liquid-permeable layer and said uppermost layer, said undulating strip of material containing colorant.

24. An absorbent article as in claim 21, a first respective portion of each said funnel-shaped opening closest to the liquid-permeable layer being wider than a second respective portion of each said funnel-shaped opening most remote from the liquid-permeable layer, thereby forcing X-Y-direction travel as well as Z-direction travel of any potential reverse wicking liquid.

25. An absorbent article as in claim 10 wherein each of said at least one take-away layer comprises discrete passages defining openings (30) extending therethrough, said discrete passages tapering inwardly toward the liquid storage layer and facilitating the absorbent article (10) in transferring liquid from the distribution layer (22) toward the liquid storage layer (24).

26. An absorbent article (10) having a front area (12) and a rear area (14), and a central area (16) between the front (12) and rear (14) areas, the absorbent article (10) comprising:

(a) a liquid-permeable layer (18) which, when the absorbent article (10) is in use, is turned toward a body of a wearer;

(b) a liquid-impermeable layer (20) which, when the absorbent article (10) is in use, is turned away from such body of such wearer;

(c) a liquid distribution layer (22) disposed between the liquid-permeable layer (18) and the liquid-impermeable layer (20), and extending from the central area (16) into at least one of the front area (12) and the rear area (14); and (d) a liquid storage layer (24) disposed between the liquid-impermeable layer (20) and the liquid distribution layer (22), the liquid storage layer extending from the front area to the rear area of said absorbent article, the liquid storage layer having a higher liquid retention capacity per unit area of said absorbent article in the respective at least one of the front area and the rear area of the absorbent article, than in the central area, the liquid distribution layer (22) comprising a major surface, which defines multiple open flow channels which promote liquid flow in a longitudinal direction toward the front (12) and/or rear (14) areas, further characterized in that the liquid distribution layer facilitates transfer of liquid longitudinally along the surface of the liquid distribution layer (22), and toward the liquid-impermeable layer (20), to at least part of the liquid storage layer (24*a*) which is located in one or both of the front area (12) and the rear area (14) of the absorbent article (10).

* * * * *